United States Patent

Kado et al.

Patent Number: 5,411,976
Date of Patent: May 2, 1995

[54] NEW THIAZOLIDINE DERIVATIVES, PROCESS FOR PREPARING SAME AND ANTI-AMNESTIC COMPOSITION CONTAINING SAME

[75] Inventors: Kunio Kado; Toshizo Shiga, both of Tokyo, Japan

[73] Assignee: Kabushiki Kaisha Yakult Nonsha, Tokyo, Japan

[21] Appl. No.: 810,447

[22] Filed: Dec. 19, 1991

Related U.S. Application Data

[63] Continuation of Ser. No. 492,333, Mar. 12, 1990, abandoned, which is a continuation of Ser. No. 288,245, Dec. 22, 1988, abandoned.

[30] Foreign Application Priority Data

Dec. 25, 1987 [JP] Japan .................. 62-327181

[51] Int. Cl.$^6$ .................. C07D 417/06; A61K 31/425
[52] U.S. Cl. .................. 514/365; 548/200
[58] Field of Search .................. 548/200; 514/365

[56] References Cited

U.S. PATENT DOCUMENTS

| | | | |
|---|---|---|---|
| 4,687,778 | 8/1987 | Tsuru | 514/419 |
| 4,857,537 | 8/1989 | Toda | 514/365 |

FOREIGN PATENT DOCUMENTS

| | | | |
|---|---|---|---|
| 0154353 | 9/1985 | European Pat. Off. . | |
| 154353 | 9/1985 | European Pat. Off. | 548/200 |
| 280956 | 9/1988 | European Pat. Off. | 548/200 |
| 0303434 | 2/1989 | European Pat. Off. . | |
| 0172929 | 9/1985 | Japan . | |
| 2270557 | 11/1987 | Japan . | |

OTHER PUBLICATIONS

T. C. Friedman et al., J. Neurochem., vol. 42, pp. 237–241, (1984).
M. Manri et al., Folio Pharmacol., Japon, vol. 89, pp. 323–329, (1987).
K. Taira et al., Folio Pharmacol., Japon, vol. 89, pp. 243–252, (1987).
T. Yoshimoto et al., J. Pharmacobio-Dyn., vol. 10, pp. 730–735, (1987).
D. Tsuru et al., Journal of Biochemistry, vol. 104, No. 4, pp. 580–586, (1988).

*Primary Examiner*—Robert Gerstl
*Attorney, Agent, or Firm*—Birch, Stewart, Kolasch & Birch

[57] ABSTRACT

New thiazolidine derivatives of the general formula:

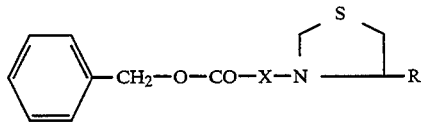

wherein X stands for a proline or thioproline residue and R for —CH$_2$OH or —CHO, a process for preparing the same which comprises reacting N-benzyloxycarbonyl-L-proline or —L-thioproline with L-thioprolinol and, if necessary, oxidizing the resultant N-benzyloxycarbonyl-L-prolyl-L-thioprolinol or —L-thioprolyl-L-thioprolinol to the corresponding thioprolinal compound, and an anti-amnestic composition containing at least one of the thiazolidine derivatives together with a conventional excipient. The new thiazolidine derivatives are extremely strong in anti-amnestic activity when compared with known similar anti-amnestic agents.

5 Claims, No Drawings

NEW THIAZOLIDINE DERIVATIVES, PROCESS FOR PREPARING SAME AND ANTI-AMNESTIC COMPOSITION CONTAINING SAME

This application is a continuation of application Ser. No. 07/288,245, filed on Dec. 22, 1988 (now abandoned), the entire contents of which are incorporated herein by reference.

BACKGROUND OF THE INVENTION

1. Field of the Invention

The present invention relates to new thiazolidine derivatives possessing very strong an anti-amnestic activity, a process for preparing same and an anti-amnestic composition containing at least one of the thiazolidine derivatives together with a conventional excipient. More particularly, the present invention relates to 3-(N-benzyloxycarbonyl)-prolyl- or -thioprolyl-4-formyl or hydroxymethyl-thiazolidine, a process for preparing same by reacting 4-benzyloxycarbonyl-proline or -thioproline with thioprolinol and, if necessary, oxidizing the resultant 4-hydroxymethyl-thiazolidine compound to the corresponding 4-formyl-thiazolidine compound, and an anti-amnestic composition containing the thiazolidine compound together with a conventional excipient. As 4-hydroxymethyl and 4-formyl thiazolidines are derived from proline by reduction and are called thioprolinol and thioprolinal, respectively, the nomenclatures of prolinol and prolinal will be used hereinafter for mentioning the compound names concretely in place of the corresponding thiazolidine compounds. However, the compounds of this invention are generally designated herein as the thiazolidine derivatives.

2. Description of the Prior Art

In recent years, some prolinal derivatives are reported as having an inhibitory activity to a physiological role of an enzyme in neuropeptide metabolism. For example, T.C. Friedman et al. reported in *J. Neurochem.* 42, 237(1984) that N-benzyloxycarbonyl-L-prolyl-L-prolinal (Z-pro-prolinal) exhibited in vivo an inhibitory activity to prolyl endopeptidase. In M. Nanri et al., Folia Pharmacol. japon, 89, 323–329(1987) and K. Taira et al., ibid. 89, 243–252, there is described that some prolinal derivatives exhibit an inhibitory activity to prolyl endopeptidase in experiments using mice as test animal and the use of these derivatives has possibility for the remedy of senile dementia. A similar report is seen in T. Yoshimoto et al., J. Pharmaco bio-Dyn., 10, 730–735(1987). Further, Japanese Laid-open Patent Appln. No. Sho. 60-172929 discloses that Z-glycyl-L-prolyl-chloromethane or -diazomethane has an inhibitory activity to prolyl endopeptidase and is utilizable as anti-amnestic agent. In Japanese Laid-open Patent Appln. No. Sho. 60-188317, there is disclosed that a prolinal which is N-substituted by an amino acid has an inhibitory activity to prolyl endopeptidase and can thus be used as an anti-amnestic agent. Furthermore, Japanese Laid-open Patent Appln. No. Sho. 62-270557 discloses a new process for preparing Z-proprolinal. However, the inhibitory activity to prolyl endopeptidase of these prolinal derivatives is still unsatisfactory in practical level, and so there is a great demand to develop new compounds which exhibit a very strong inhibitory activity to prolyl endopeptidase.

BRIEF SUMMARY OF THE INVENTION

Accordingly, it is an object of the present invention to provide new thiazolidine derivatives possessing a strong valuable pharmacological property.

It is another object of the present invention to provide a process for the preparation of the new thiazolidine derivatives according to a series of methods known per se.

It is still another object of the present invention to provide a new type anti-amnestic composition comprised of at least one of the new thiazolidine derivatives.

It is a further object of the present invention to provide a method for using the new anti-amnestic composition for the remedy of memory disorders.

Other objects, features and advantages of the present invention will be apparent more fully from the following description.

DETAILED DESCRIPTION OF THE INVENTION

As a result of extensive research made by the present inventors for developing a new amnestic agent, it has now been found that a new class of thiazolidine derivatives which are characterized by containing in their molecule thioprolinol or thioprolinal and a prolyl or thioprolyl group in a tandem structure exhibit an extremely strong anti-amnestic activity as compared with known similar anti-amnestic compounds. The present invention has been accomplished on the basis of the above finding.

In accordance with one embodiment of the present invention, there is provided new thiazolidine derivatives of the general formula:

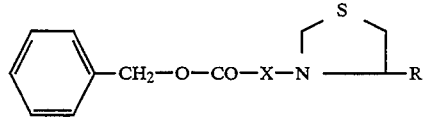

wherein X stands for a proline or thioproline residue and R for —CH$_2$OH or —CHO.

In accordance with another embodiment of the present invention, there is provided a process for the preparation of new thiazolidine derivatives of the general formula:

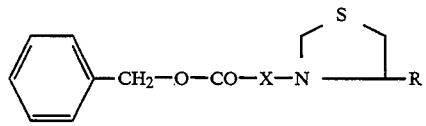

wherein X stands for a proline or thioproline residue and R for —CH$_2$OH or —CHO, which comprises reacting N-benzyloxycarbonyl-L-proline or -L-thioproline with L-thioprolinol and, if necessary, oxidizing the resultant N-benzyloxycarbonyl-L-prolyl-L-thioprolinol or -L-thioprolyl-L-thioprolinol with an oxidizing agent to N-benzyloxycarbonyl-L-prolyl-L-thioprolynal or -L-thioprolyl-L-thioprolinal.

In accordance with still another embodiment of the present invention, there is provided an anti-amnestic composition which comprises as an active ingredient thereof at least one thiazolidine derivative of the general formula:

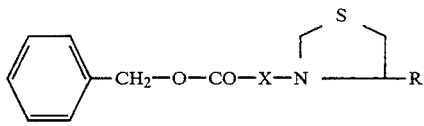

wherein X stands for a proline or thioproline residue and R for —CH$_2$OH or —CHO, in a pharmacologically active amount together with a conventional excipient.

The new thiazolidine derivatives of the above general formula are prepared in a manner known per se, for example, by reacting N-benzyloxycarbonyl-L-proline or -L-thioproline with L-thioprolinol to form a compound of the general formula wherein R is the grouping —CH$_2$OH, and if necessary, oxidizing this compound with an oxidizing agent to form a compound of the general formula wherein R is the grouping —CHO.

N-Benzyloxy-L-proline or -L-thioproline and L-thioprolinol used in the process of this invention as starting materials are known or can be prepared in a manner known per se. For example, N-benzyloxycarbonyl-L-proline or -L-thioproline can be prepared by acylating L-proline or L-thioproline with benzyl chlorocarbonate. L-Thioprolinol is commercially available but may be prepared by reducing L-thioproline with a carbonyl-reducing agent such as sodium borohydride or lithium aluminum hydride in a manner known per se.

The reaction between N-benzyloxycarbonyl-L-proline or -L-thioproline with L-thioprolinol is carried out normally in a proper solvent such as methylene chloride or chloroform in the presence of 1,3-dimethyl-2-chloroimidazolinium chloride and a tertiary amine such as triethylamine. The resultant N-benzyloxycarbonyl-L-prolyl-L-thioprolinol or -L-thioprolyl-L-thioprolinol can be purified by recrystallization from a solvent such as ether.

The alcohol moiety, —CH$_2$OH, of the resultant N-benzyloxycarbonyl-L-prolyl-L-thioprolinol or -L-thioprolyl-L-thioprolinol can be oxidized, if necessary, with an oxidizing agent to the corresponding prolinal or thioprolinal compound having the group —CHO in place of —CH$_2$OH. As the oxidizing agent in this case, phosgen is used under cooling in the presence of dimethylsulfoxide and a tertiary amine such as triethylamine. The resultant N-benzyloxycarbonyl-L-prolyl-L-thioprolinal or -L-thioprolyl-L-thioprolinal can be purified by column chromatography on silica gel using chloroform-methanol (50:1) as eluent.

The end product of this invention may be prepared in another way for example, by performing the same reaction as above but starting with a proline or thioproline having an N-protecting acyl Group, e.g. N-tert-butyloxycarbonyl-L-proline or -thioproline and finally saponifying the N-acyl group in the resultant N-acyl-L-prolyl-L-thioprolinol or -L-thioprolyl-L-thioprolinol with an alkali and acylating the saponified compound with a benzyloxycarbonyl halide in the presence of a base.

The new thiazolidine derivatives of the present invention are extremely strong in anti-amnestic activity as compared with similar known anti-amnestic agents as will be evident from comparative tests given hereinafter. Thus, the thiazolidine derivatives of the present invention can be used as a strong anti-amnestic agent. Accordingly, the present invention is also concerned with an anti-amnestic composition containing at least one of the thiazolidine derivative or derivatives in a pharmacologically active amount together with a conventional excipient. The present invention is further concerned with the use of the anti-amnestic composition lot the remedy of memory disorders of human, for example, senile dementia of the Alzheimer's type.

The thiazolidine derivatives of the general formula wherein R is the grouping —CHO (thioprolinal derivatives) ate very strong in inhibitory activity and as such are useful as medicaments for the remedy of memory disorders. However, the thiazolidine derivatives of the general formula wherein R is the grouping —CH$_2$OH (thioprolinol derivatives) are not strong in vitro in the inhibitory activity. Thus, these thiazolidine derivatives (thioprolinol derivatives) can be regarded as useful intermediate products for the preparation of the derivatives of the general formula wherein R is the grouping —CHO (thioprolinal derivatives). However, these thioprolinol derivatives ate converted in vivo into the thioprolinal derivatives having strong anti-amnestic effect.

The thiazolidine derivatives of the present invention can be administered to patients in various ways such as by injection, for example, intravenous, subcutaneous or intramuscular injection and chewable, water-dispersible or drinkable preparations suitable for oral administration. In general, the thiazolidine derivatives are used singly or may be used as a mixture of at least two. On administration to patients, the thiazolidine derivatives are normally blended with a suitable excipient usually employed for pharmaceutical formulations. An excipient utilizable for this purpose includes one or more organic and inorganic substances which are suitable for enteral or parenteral administration and do not react with the thiazolidine derivatives of the general formula, for example, water, vegetable oils, benzyl alcohol, polyethylene glycols, gelatin, carbohydrates such as lactose and starch, magnesium stearate, talc or white petroleum jelly. Other organic and inorganic substances usually employed for preparing various medicaments can also be used as the excipient unless they do not influence the effect of the prolinal derivatives. The formulations used for oral administration must easily be absorbed in digestive organs and are, in particular, powders, tablets, pills, dragees, hard and soft capsules, syrups, juices, drops, elixirs and other orally acceptable liquid preparations, preferably oily or aqueous solutions, suspensions and emulsions. The formulations for various types of injection preparations are as a rule in the form of the above liquid preparations. For injection, the thiazolidine derivatives may be lyophilized and the resulting lyophilizate may be used for such injection preparations. The indicated formulations can be sterilized and/or contain one or more auxiliary substances such as lubricants, preservatives, stabilizers and/or wetting agents, emulsifiers, salts for influencing the osmotic pressure, buffer substances, dyestuffs, flavoring agents and/or aroma substances. They can also contain, if desired, one or more further active compounds, for example, lecithin, one or more vitamins, and depressants.

Particularly preferable as a mode of administration of the thiazolidine derivatives are oral administration and intravenous injection. The daily dose of the thiazolidine derivatives is preferably between 1 mg and 900 mg/Kg, especially between 5 mg and 500 mg/Kg of body weight in case of oral administration and between 0.5 mg and 500 mg/Kg, especially between 1 mg and 200 mg/Kg of body weight in case of intravenous injection. The particular dose for each specific patient depends, however, on very diverse factors, for example, the effectiveness of the particular thiazolidine derivative employed, the age, the body weight, the general state of health and the sex, the diet, the time and mode of administration, the rate of elimination, the combination of medicaments and the severity of the particular ailment to which the remedy applies. In the anti-amnestic composition of the present invention, the thiazolidine derivative or derivatives as active ingredient are contained generally in a concentration of 0.1% or more, preferably 1–50% by weight.

Described below are the inhibitory action of the thiazolidine derivatives of the present invention to prolylenepeptidase and the anti-amnestic effect of the thiazolidine derivatives on rats according to a step-down type passive avoidance test.

(1) Inhibitory activity of the thiazolidine derivatives to prolylendpeptidase in terms of 50% inhibitory concentration ($IC_{50}$)

The inhibitory activity of the thiazolidine derivatives of the present invention is shown below in terms of 50% inhibitory concentration ($IC_{50}$) in comparison with the known conventional anti-amnestic agent.

Inhibitory activity to prolylendpeptidase $IC_{50}$.

Compound

N-Benzyloxycarbonyl-L-prolyl-L-prolinal (control) 0.74

N-Benzyloxycarbonyl-L-prolyl-L-thioprolinal (Example 2) 1.6

N-Benzyloxycarbonyl-L-thioprolyl-L-thioprolinal- (Example 4) 0.0013

N-Benzyloxycarbonyl-L-thioprolyl-L-thioprolinol (Example 3) 600000

In view of the tabulated result, it is noted that N-benzyloxycarbonyl-L-thioprolyl-L-thioprolinal (Example 4) of the present invention is about 600 times as high in inhibitory activity as N-benzyloxycarbonyl-L-prolyl-L-prolinal used as control. N-Benzyloxycarbonyl-L-thioprolyl-L-thioprolinol (Example 3) of the present invention is not effective in vitro but this compound as an intermediate compound of N-benzyloxycarbonyl-L-thioprolyl-L-thioprolinal (Example 4) is oxidized in vivo to an aldehyde form, i.e. the compound of Example 4, exhibiting a satisfactory inhibitory effect.

(2) A step-down type passive avoidance test

This test was carried out by using the undermentioned apparatus (A) and test animal (B) according to the undermentioned testing method (C).

(A) Test chamber for passive avoidance response of rats

A test chamber of 200(w)×200(1) mm in area was made of transparent acrylic resin plates for observation of the inside and was provided on one side thereof with an electrically insulated platform of 150(w)×200(1)×40(h) in size and on the bottom with a grid floor made of stainless steel which was equipped with a foot-shock generator/scrumbler (HASG-101/S, Medical Agent, Inc.) capable of sending electric current to the grid floor for giving a test animal electric foot shock.

(B) Test animal

5-Weeks-old male rats of Wister strain weighing 100–145 g (Japan Clea Co., Ltd.) were used as test animals.

(C) Testing method

The passive avoidance test consists of two steps; an acquisition trial and a retention trial. The thiazolidine derivative of the present invention was dissolved in saline and intraperitoneally administered to the rats in a dose of 2.2 mg/kg body weight one hour before the acquisition trial. As control, only saline was administered intraperitoneally to a group of the rats. In the acquisition trial, the rat was placed on the platform in the test chamber and, when the rat stepped down on the floor, the electric current of 4 mA was immediately sent to the grid continuously until the rat went up on the platform. At the time the rat having gone up on the platform stayed there for more than 20 seconds, the rat was regarded to have learned the situation and taken out of the test chamber. Repeating this test with another rat under the same condition, the rats learned the situation were collected as passing the test for the acquisition trial. A total time of measurement in the acquisition trial was limited to 300 seconds as maximum, and the time elapsing until the rat stepped down to the grid floor (step-down latency, SDL), the total time elapsing until the rat learned the situation and the times of step-down were measured. In order to avoid any significant difference in the rats, those required more than 300 seconds for the first step-down to the grid floor, those stepped down to the floor at least 5 times and those failed to learn the situation within 300 seconds were excluded. Immediately after the acquisition trial, scopolamine hydrobromide (SCOP) dissolved in saline was administered intraperitoneally in a dose of 3.0 mg/kg of body weight to the rat to prepare a SCOP-induced amnestic rat. As control, only saline was administered intraperitoneally to a group of the rats. The retention trial was carried out by putting the rat on the platform of the test chamber after the lapse of 24 and 48 hours from the acquisition trial, and the time elapsing until the rat went down to the floor (SDL) was measured. A statistical treatment of the data obtained was made according to the Student's t-test. A result of the test is shown in the table below.

| | | | | Acquisition trial | | | Retention trial | | |
|---|---|---|---|---|---|---|---|---|---|
| | | Type of | Treatment | Step-down | Number of | Total time | Step-down latency | | Number |
| Test compound | Dose (mg/kg) | administration | after learning | latency (sec) | step-down (times) | for the test (sec) | After 24 hours | After 48 hours | of rats |
| Saline | — | i.p. | Saline | 13.5 | 2.5 | 75.2 | 288.8 | 213.2 | 10 |
| Saline | — | i.p. | Scopolamine | 10.7 | 2.2 | 56.0 | 138.7 | 148.2 | 10 |
| N-Benzyloxycarbonyl-L-thioprolyl-L-thioprolinal (Example 4) | 2.2 | i.p. | Scopolamine | 7.6 | 2.0 | 52.1 | 170.9 | 176.5 | 11 |
| N-Benzyloxycarbonyl-L-thioprolyl-L-thioprolinal (Example 4) | 11.0 | i.p. | Scopolamine | 8.9 | 2.2 | 57.1 | 245.7* | 177.0 | 11 |

-continued

Anti-amnestic effect of the test compounds on rats by intraperitoneal administration

| Test compound | Dose (mg/kg) | Type of administration | Treatment after learning | Acquisition trial | | | Retention trial | | Number of rats |
| --- | --- | --- | --- | --- | --- | --- | --- | --- | --- |
| | | | | Step-down latency (sec) | Number of step-down (times) | Total time for the test (sec) | Step-down latency | | |
| | | | | | | | After 24 hours | After 48 hours | |
| N-Benzyloxycarbonyl-L-thioprolyl-L-thioprolinol (Example 3) | 2.2 | i.p. | Scopolamine | 9.8 | 2.4 | 67.5 | 238.2* | 174.0 | 11 |

Remarks: Significantly different from SCOP-treated group (Student's t-test).
*p<0.05
**p<0.01
i.p.: intraperitoneal The present invention will now be illustrated by way of Examples wherein DMC and DMSO are abbreviations of 1,3-dimethyl-2-chloroimidazolinium chloride and dimethyl sulfoxide, respectively, and the percentage is by weight unless otherwise indicated.

EXAMPLE 1

Preparation of N-benzyloxycarbonyl-L-prolyl-L-thioprolinol (1) Preparation of L-thioprolinol In 900 ml of anhydrous ethanol was suspended 33.8 g of $CaCl_2$ and the suspension was cooled below $-25°$ C. To this suspension kept below $-25°$ C. was added dropwise in 60 minutes under agitation 1400 ml of an ethanolic solution of 11.9 g of $NaBH_4$. After stirring the mixture for 20 minutes, 300 ml of an ethanolic solution of 60 g of L-thioproline ethyl ester kept below $-25°$ C. was added dropwise to the mixture under agitation and the admixture was stirred overnight below $-20°$ C. At room temperature, 60 ml of HCl was added in small portions to the mixture and the whole was concentrated under reduced pressure until dryness. The residue was taken up with an appropriate amount of water and the aqueous solution was washed with chloroform. The solution was then treated with $NaHCO_3$ to adjust the pH value to 8 and then filtered. The filtrate was extracted 20 times in total with a total amount of 1000 ml of chloroform. The chloroform extracts except those up to 3 times were collected, dried with $MgSO_4$ and filtered. The filtrate was concentrated under reduced pressure and the product was precipitated twice with hexane and then dried under reduced pressure.

m.p.: 90° C., $[\alpha]D^{25.5°}$ $^{C.}=-20.41$, $\alpha=-0.098$.
Yield: 22 g (59.6%).

(2) Preparation of N-benzyloxycarbonyl-L-prolyl-L-thioprolinol

In 700 ml of methylene chloride were dissolved 24.9 g of N-benzyloxycarbonyl-L-proline, 42 ml of triethylamine and 11.9 g of L-thioprolinol prepared in (1). To this solution was added dropwise in 60 minutes under agitation below 25° C. 26.0 g of DMC in 300 ml of methylene chloride. The mixture was then washed successively with water, a saturated aqueous solution of sodium hydrogen carbonate, 1N-HCl and water, dried with $MgSO_4$ and filtered. The filtrate was concentrated until dryness under reduced pressure and the residue was crystallized with ether whereby the end product was obtained.

m.p.: 140° C., $[\alpha]D^{26°}$ $^{C.}=-38.56$ ($CHCl_3$), $\alpha=-0.193$
Yield: 30.9 g (85%)

EXAMPLE 2

Preparation of N-benzyloxycarbonyl-L-prolyl-L-thioprolinal

To 150 ml of methylene chloride was added at $-60°$ C. under agitation 7.8 ml of phosgen in nitrogen atmosphere. To this mixture was then added dropwise in 60 minutes under agitation 150 ml of methylene chloride solution of DMSO 14.7 ml. After stirring the mixture continuously for 5 minutes, 15 g of N-benzyloxycarbonyl-L-prolyl-L-thioprolinol obtained in Example 1 in 200 ml of methylene chloride was added dropwise in 40 minutes to the mixture under agitation, and the mixture was then stirred for further 30 minutes. To the mixture was added dropwise 57.2 ml of triethylamine, and the mixture was stirred until the temperature of the mixture became room temperature. After washing the mixture with water and a saturated aqueous solution of edible salt, the mixture was dried with MgSO and filtered. The filtrate was concentrated until dryness under reduced pressure, 60 ml of ethanol, 45 g of sodium hydrogen sulfate and 80 ml of water were added to the residue and the mixture was stirred for 15 minutes. The ethanol was distilled off and the mixture was extracted twice with chloroform. The extracts were washed with a saturated aqueous solution of sodium hydrogen carbonate and then water, dried over $MgSO_4$ and filtered. The filtrate was concentrated under reduced pressure until dryness and the residue was subjected to column chromatography on silica gel, using chloroform-methanol (50:1) as solvent. The eluent was concentrated under reduced pressure until dryness. To the residue were added 30 ml of ethanol, 45 g of sodium hydrogen sulfate and 80 ml of water and the mixture was stirred. The ethanol was removed by distillation and the residual liquid was washed 3 times with ether. The aqueous layer was treated with an aqueous solution of sodium carbonate to adjust the pH to 9, and the mixture was extracted twice with chloroform, dried over $MgSO_4$ and filtered. The filtrate was concentrated until dryness under reduced pressure whereby the end product was obtained in an oily form.

$\alpha=-0.077$, $[\alpha]D^{23.5°}$ $^{C.}=-15.70$ ($CHCl_3$)
Yield: 5.2 g (34.7%).

EXAMPLE 3

Preparation of N-benzyloxycarbonyl-L-thioprolyl-L-thioprolinol (1) Preparation of N-benzyloxycarbonyl-L-thioproline In 94 ml of 2-N NaOH was dissolved 25 g of L-thioproline, and 20 ml of ether was added to the solution under agitation and ice-cooling. To this solution under agitation were added dropwise 38 ml of benzyloxycarbonyl chloride and 70 ml of 4-N NaOH at the same time in 30 minutes. The mixture was stirred for 2 hours at room temperature, washed with 100 ml of ether and treated with 6-N HCl to adjust pH to 2. The mixture was extracted with 200 ml and 100 ml of ethyl acetate and the ethyl acetate phase was washed 50 ml of water, dried over MgSO$_4$ and filtered. The filtrate was concentrated until dryness under reduced pressure whereby an oily substance was obtained.

Yield: 51 g (100%).

(2) Preparation of N-benzyloxycarbonyl-L-thioprolyl-L-thioprolinol

In 700 ml of methylene chloride were dissolved with stirring at room temperature 29 g of the oily substance obtained in (1), 45 ml of triethylamine and 12.9 g of L-thioprolinol obtained in Example 1-(1). To this solution was added dropwise in one hour 30 g of DMC in 330 ml of methylene chloride. The mixture was stirred for one hour at room temperature and washed successively with water, a saturated aqueous solution of sodium hydrogen carbonate, 1-N HCl and water. The methylene chloride phase was dried over MgSO$_4$ and filtered. The filtrate was concentrated until dryness under reduced pressure and the residue was crystallized from ether whereby the end product was obtained.

m.p.: 127° C., $[\alpha]D^{25°\ C.} = -129.77$ (CHCl$_3$)

Yield: 34 g (85.2%).

EXAMPLE 4

Preparation of N-benzyloxycarbonyl-L-thioprolyl-L-thioprolinal

To 150 ml of methylene chloride was added at −60° C. under agitation 7.5 ml of phosgen in nitrogen atmosphere. To this mixture was then added dropwise in 60 minutes under agitation 150 ml of methylene chloride solution of DMSO 6.2 ml. After stirring the mixture continuously for 5 minutes, 16 g of N-benzyloxycarbonyl-L-thioprolyl-L-thioprolinol obtained in Example 3 in 200 ml of methylene chloride was added dropwise in 40 minutes to the mixture under agitation, and the mixture was then stirred for further 30 minutes. To the mixture was added dropwise 55 ml of triethylamine, and the mixture was stirred until the temperature of the mixture became room temperature. After washing the mixture twice with water, the mixture was dried over MgSO$_4$ and filtered. The filtrate was concentrated until dryness under reduced pressure, and the residue was subjected to column chromatography on silica gel, using chloroform-methanol (50:1) as solvent. The eluent was concentrated under reduced pressure until dryness. To the residue were added 41 ml of ethanol, 48 g of sodium hydrogen sulfate and 84 ml of water and the mixture was stirred for 15 minutes. The ethanol was removed by distillation and the residual liquid was washed with ether. The aqueous phase was treated with an aqueous solution of potassium carbonate to adjust the pH to 9, and the mixture was extracted with 200 ml of chloroform. The extract was dried over MgSO$_4$ and filtered. The filtrate was concentrated until dryness under reduced pressure whereby the end product was obtained in oily form (semi-solid).

$[\alpha]D^{20°\ C.} = -102.20$ (CHCl$_3$)

Yield: 6.1 g (38.3%)

The following examples illustrate the preparation of the anti-amnestic compositions of the present invention. It is to be construed, however, that the preparation of the anti-amnestic compositions of the present invention is not limited to these examples.

EXAMPLE A

Injection Preparations (1) Recipe

| | |
|---|---|
| N-Benzyloxycarbonyl-L-prolyl-L-thioprolinal | 10 mg |
| Hardened castor oil polyoxyethylene 60 mol ether | 40 mg |
| Sorbitan monostearate | 2 mg |
| Propylene glycol | 60 mg |
| Refined soybean lecitin | 2 mg |
| Cholesterol | 1 mg |
| Dextrose | 50 mg |
| Distilled water | to make 1 ml |

(2) Preparation

N-Benzyloxycarbonyl-L-prolyl-L-thioprolinal, hardened castor oil polyoxyethylene 60 mol ether, sorbitan monostearate, propylene glycol, refined soybean lecitin and cholesterol are mixed and fused to form a homogeneous liquid in a water bath heated at about 80° C. To this liquid is added with stirring distilled water heated at about 80° C. to form a solubilized homogeneous system. Dextrose is then added and distilled water is added to make the volume of 1 ml. The liquid is subjected to sterilizing filtration, and charged into an amber ampoule which is then sealed.

EXAMPLE B

Soft capsulated preparations (1) Recipe

| | |
|---|---|
| N-Benzyloxycarbonyl-L-thioprolyl-L-thioprolinal | 20 mg |
| Macrogol 400 | 350 mg |
| Propylene glycol | 38 mg |
| Dipotassium glycyrrhizinate | 1 mg |
| Menthol oil | 1 mg |
| Gelatin | 122 mg |
| Glycerol | 30.5 mg |
| D-Sorbitol liquid | 12.2 mg |
| Ethyl p-hydroxybenzoate | 0.8 mg |
| Propyl p-hydroxybenzoate | 0.5 mg |

(2) Preparation

N-Benzyloxycarbonyl-L-thioprolyl-L-thioprolinal, Macrogol 400, dipotassium glycyrrhizinate, menthol oil and propylene glycol are homogeneously blended to form a suspension. Separately, a coating agent for soft capsules is manufactured from gelatin, glycerol, D-sorbitol liquid, ethyl p-hydroxybenzoate and propyl p-hydroxybenzoate. Using the suspension and the coating agent, a soft capsule is prepared.

It is understood that the preceding representative examples may be varied within the scope of the present specification both as to reactants, reaction conditions and ingredients to be blended, by one skilled in the art to achieve essentially the same results.

As many widely different embodiments of this invention may be made without departing from the spirit and scope thereof, it is to be construed that this invention is not limited to the specific embodiments thereof except as defined in the appended claims.

What is claimed is:

1. A thiazolidine derivative of the general formula:

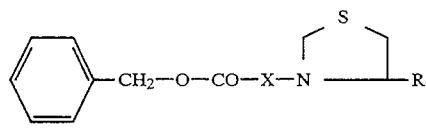

wherein X stands for a proline or thioproline residue and R stands for —CH$_2$OH or —CHO.

2. N-Benzyloxycarbonyl-L-prolyl-L-thioprolinal.

3. N-Benzyloxycarbonyl-L-thioprolyl-L-thioprolinal.

4. An anti-amnestic composition which comprises as an active ingredient thereof at least one thiazolidine derivative of the general formula

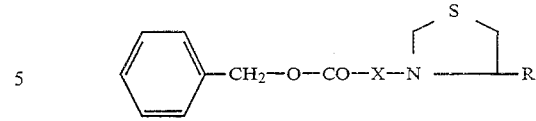

wherein X stands for a proline or thioproline residue and R stands for a —CH$_2$OH or —CHO, in a pharmacologically active amount and a conventional excipient.

5. An anti-amnestic composition according to claim 4, wherein the amount of said active ingredient is 1–50% by weight based on the weight of the composition.

* * * * *